United States Patent
Imamura

(10) Patent No.: US 10,624,608 B2
(45) Date of Patent: Apr. 21, 2020

(54) ULTRASONIC DIAGNOSTIC APPARATUS

(71) Applicant: Toshiba Medical Systems Corporation, Otawara-shi (JP)

(72) Inventor: Tomohisa Imamura, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 1189 days.

(21) Appl. No.: 14/824,788

(22) Filed: Aug. 12, 2015

(65) Prior Publication Data

US 2015/0342565 A1    Dec. 3, 2015

Related U.S. Application Data

(63) Continuation of application No. PCT/JP2014/054926, filed on Feb. 27, 2014.

(30) Foreign Application Priority Data

Feb. 28, 2013    (JP) .................................. 2013-038581

(51) Int. Cl.
  *A61B 8/00*    (2006.01)
  *A61B 8/08*    (2006.01)
  (Continued)

(52) U.S. Cl.
  CPC ............... *A61B 8/463* (2013.01); *A61B 8/06* (2013.01); *A61B 8/14* (2013.01); *A61B 8/483* (2013.01);
  (Continued)

(58) Field of Classification Search
  CPC .... A61B 8/00; A61B 8/06; A61B 8/08; A61B 8/14; A61B 8/463; A61B 8/483;
  (Continued)

(56) References Cited

U.S. PATENT DOCUMENTS 6,293,913 B1    9/2001    Tsujino et al.
6,610,014 B1    8/2003    Yamamoto et al.
(Continued)

FOREIGN PATENT DOCUMENTS

CN    101081170 A    12/2007
CN    101790351 A    7/2010
(Continued)

OTHER PUBLICATIONS

Combined Chinese Office Action and Search Report dated Sep. 5, 2016 in Patent Application No. 201480010524.7 (with English language translation of categories of cited documents).
(Continued)

*Primary Examiner* — Carolyn A Pehlke
(74) *Attorney, Agent, or Firm* — Oblon, McClelland, Maier & Neustadt, L.L.P.

(57) ABSTRACT

According to embodiment, an ultrasonic diagnostic apparatus includes transmission/reception circuitry transmitting/receiving an ultrasonic wave to/from an object via a piezoelectric transducer, ultrasonic image generation circuitry generating a series of ultrasonic images along a time series based on an output from the transmission/reception circuitry, specifying information generation circuitry generating predetermined specifying information concerning each of the series of ultrasonic images, selection circuitry selecting a color Doppler image from the series of ultrasonic images based on the specifying information in response to a predetermined operation during display of the series of ultrasonic images, and storage circuitry storing the selected color Doppler image.

5 Claims, 10 Drawing Sheets

(51) Int. Cl.
*A61B 8/14* (2006.01)
*A61B 8/06* (2006.01)
*G06T 7/00* (2017.01)

(52) U.S. Cl.
CPC .......... *A61B 8/5207* (2013.01); *A61B 8/5223* (2013.01); *A61B 8/5276* (2013.01); *A61B 8/5292* (2013.01); *G06T 7/0012* (2013.01); *A61B 8/08* (2013.01); *A61B 8/488* (2013.01)

(58) Field of Classification Search
CPC ..... A61B 8/488; A61B 8/5207; A61B 8/5223; A61B 8/5276; A61B 8/5292; G06T 7/0012
See application file for complete search history.

(56) References Cited

U.S. PATENT DOCUMENTS

| | | | |
|---|---|---|---|
| 7,578,792 B2 | 8/2009 | Lee et al. | |
| 2008/0009737 A1* | 1/2008 | Takimoto | A61B 8/06 600/454 |
| 2011/0137169 A1* | 6/2011 | Akaki | A61B 8/00 600/443 |

FOREIGN PATENT DOCUMENTS

| | | |
|---|---|---|
| CN | 103126724 A | 6/2013 |
| JP | 10-323349 A | 12/1998 |
| JP | 2001-046372 A | 2/2001 |
| JP | 2004-057356 A | 2/2004 |
| JP | 2006-325955 A | 12/2006 |
| JP | 2007-301398 A | 11/2007 |
| JP | 2010-534501 A | 11/2010 |
| WO | WO 2009/013686 A2 | 1/2009 |

OTHER PUBLICATIONS

International Search Report dated Apr. 1, 2014 for PCT/JP2014/054926 filed Feb. 27, 2014 with English Translation.
International Written Opinion dated Apr. 1, 2014 for PCT/JP2014/054926 filed Feb. 27, 2014.
Office Action dated Dec. 7, 2018 in corresponding Chinese Patent Application No. 201480010524.7, 26 pages.

* cited by examiner

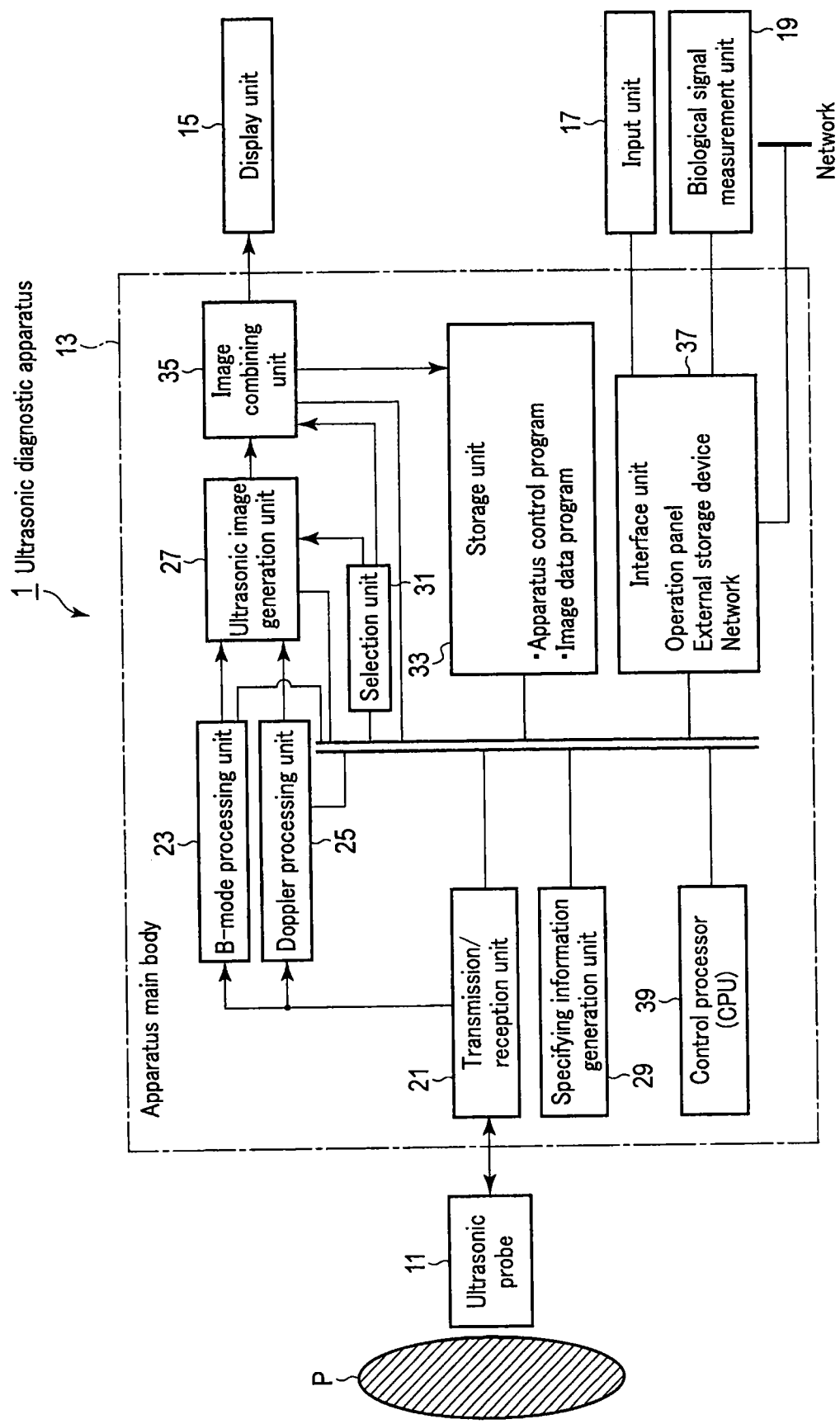
F I G. 1

| Specifying information |
|---|
| Color image information (sufficient amount of blood flow)<br>• Number of color pixels of color blood flow image<br>• Intensity of power blood flow image |
| B-mode image information<br>(motion amount in scanned region concerning B-mode images between frames)<br>• Motion vectors in scanned region (motion vector field) |
| Blood flow information<br>• Maximum flow velocity time corresponding to maximum flow velocity value on Doppler waveform<br>• Average flow velocity value near sample gate on color blood flow image |
| Biological information<br>• Biological signal waveform<br>(R-wave of electrocardiographic waveform, I sound of phonocardiographic waveform, and a-wave of acceleration sphygmographic wave on sphygmographic waveform) |
| Measurement cursor<br>• Measurement cursor set time when measurement cursor is set on Doppler waveform |

FIG. 2

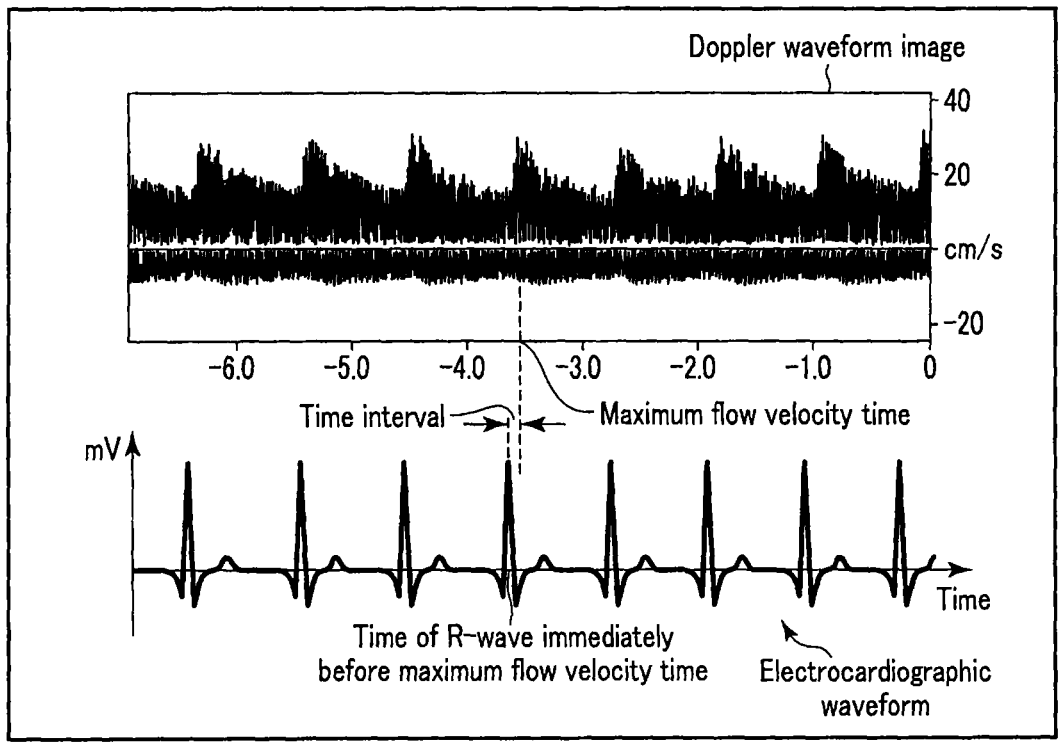

FIG. 3

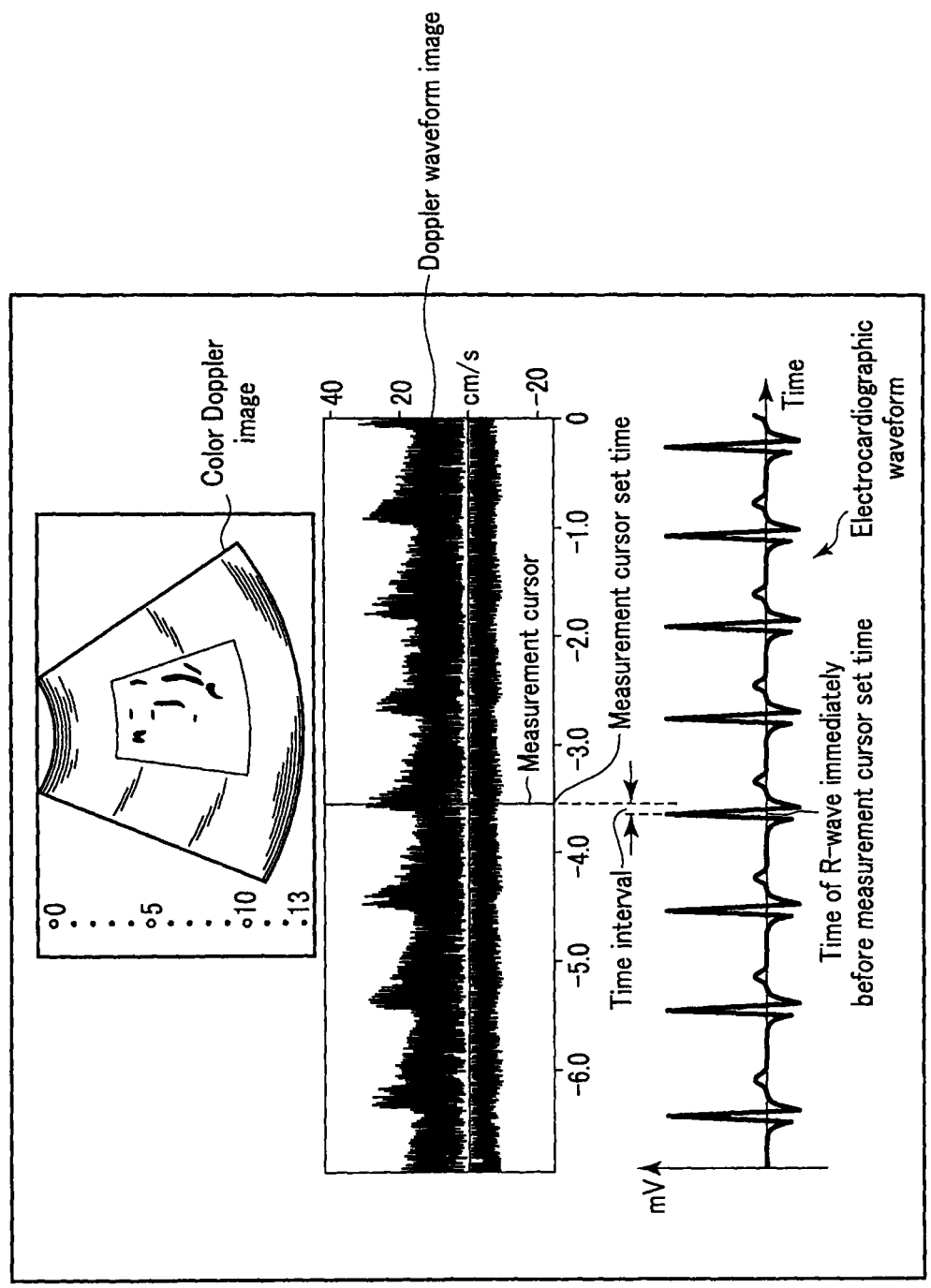
F I G. 4

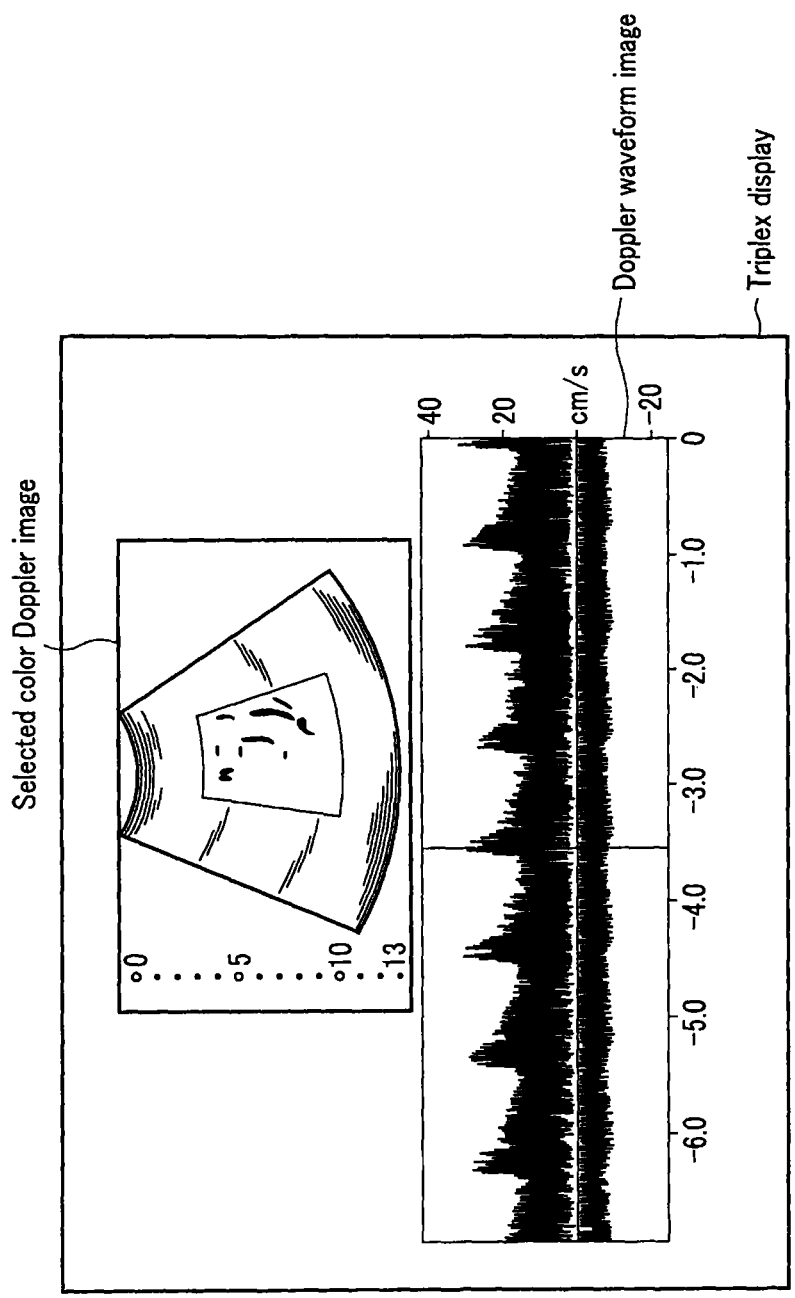
F I G. 5

ULTRASONIC DIAGNOSTIC APPARATUS

CROSS-REFERENCE TO RELATED APPLICATIONS

This application is a Continuation application of PCT Application No. PCT/JP2014/054926, filed Feb. 27, 2014 and based upon and claims the benefit of priority from the Japanese Patent Application No. 2013-038581, filed Feb. 28, 2013, the entire contents of all of which are incorporated herein by reference.

FIELD

Embodiments described herein relate generally to an ultrasonic diagnostic apparatus.

BACKGROUND

Conventionally, an ultrasonic diagnostic apparatus has a function of acquiring Doppler waveforms by, for example, the pulse Doppler method, when displaying a color Doppler image, in response to the input of the operation of generating Doppler waveforms or updating Doppler waveforms or a freeze operation (which operation will be referred to as a predetermined operation hereinafter). At this time, the updating of a color Doppler image is stopped. In addition, the ultrasonic diagnostic apparatus stores the frozen color Doppler image and then stores the frozen color Doppler image.

However, as shown in FIG. 9, the frozen color Doppler image is not sometimes optimal for the operator. A cause of this is that, for example, the respiration and pulsation of an object, the shaking of the hand of the operator who holds the ultrasonic probe, and the like influence a color Doppler image. At this time, the operator can manually select an optimal color Doppler image. However, the manual selection of a color Doppler image is cumbersome to the operator, and sometimes degrades examination efficiency. In addition, a frozen color Doppler image is sometimes stored in a state unsuitable for recording.

BRIEF DESCRIPTION OF THE DRAWINGS

FIG. 1 is a block diagram showing the arrangement of an ultrasonic diagnostic apparatus according to the first embodiment.

FIG. 2 is a view showing an example of a list of specifying information generated by a specifying information generation unit according to the first embodiment.

FIG. 3 is a view showing the maximum flow velocity time, the time of an R-wave, and the time interval on the electrocardiogram displayed together with a Doppler waveform image according to the first embodiment.

FIG. 4 is a view showing the measurement cursor set time, the time of the R-wave, and the time interval on the electrocardiogram displayed together with triplex display according to the first embodiment.

FIG. 5 is a view showing a selected color Doppler image together with a Doppler waveform image according to the first embodiment.

DETAILED DESCRIPTION

Figure 6:
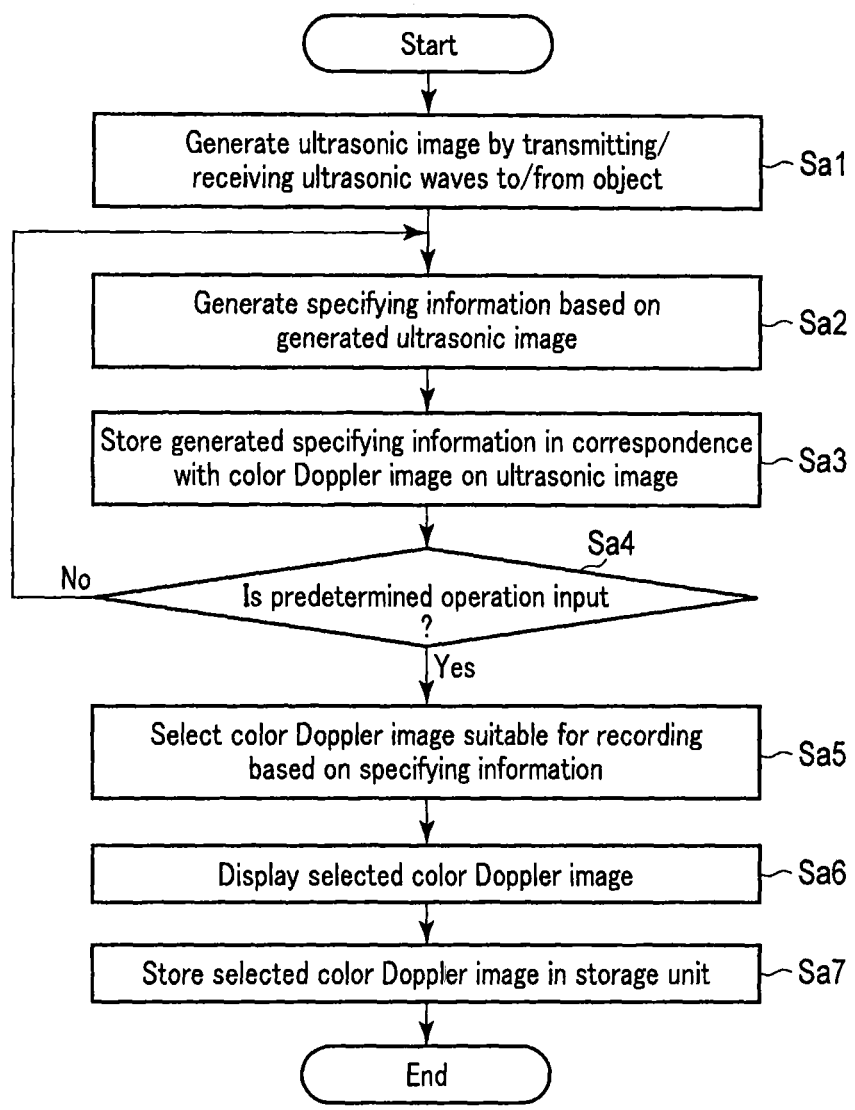
FIG. 6 is a flowchart showing an example of a procedure for color Doppler image selection processing according to the first embodiment.

In general, according to one embodiment, an ultrasonic diagnostic apparatus includes transmission/reception circuitry, ultrasonic image generation circuitry, specifying information generation circuitry, selection circuitry, and storage circuitry.

The transmission/reception circuitry transmits/receives an ultrasonic wave to/from an object via a piezoelectric transducer.

The ultrasonic image generation circuitry generates a series of ultrasonic images along a time series based on an output from the transmission/reception circuitry.

The specifying information generation circuitry generates predetermined specifying information concerning each of the series of ultrasonic images.

The selection circuitry selects a color Doppler image from the series of ultrasonic images based on the specifying information in response to a predetermined operation during display of the series of ultrasonic images.

The storage circuitry stores the selected color Doppler image.

Ultrasonic diagnostic apparatuses according to the embodiments will be described below with reference to the accompanying drawings. Note that the same reference numerals in the following description denote constituent elements having almost the same arrangements, and a repetitive description will be made only when required.

First Embodiment

FIG. 1 is a block diagram showing the arrangement of an ultrasonic diagnostic apparatus 1 according to the first embodiment. As shown in FIG. 1, the ultrasonic diagnostic apparatus 1 includes an ultrasonic probe 11, an apparatus main body 13, a display unit 15, and an input unit 17 which is connected to the apparatus main body 13 and inputs various types of instructions, commands, and information from the operator to the apparatus main body 13. In addition, a biological signal measurement unit 19 typified by an electrocardiograph, a phonocardiograph, sphygmograph, or the like and a network may be connected to the ultrasonic diagnostic apparatus 1 via an interface unit 37. The biological signal measurement unit 19 measures a biological signal waveform concerning an object. The biological signal measurement unit 19 outputs the measured biological signal waveform to the apparatus main body 13 via the interface unit 37 (to be described later). The biological signal measurement unit 19 is, for example, an electrocardiograph, a phonocardiograph, sphygmograph, or the like.

The ultrasonic probe 11 includes a plurality of piezoelectric transducers, a matching layer, and a backing member provided on the rear surface side of the plurality of piezoelectric transducers. The plurality of piezoelectric transducers are acoustoelectric reversible conversion elements such as piezoelectric ceramic elements. The plurality of piezoelectric transducers are arranged in parallel and mounted on the distal end of the ultrasonic probe 11. Assume that in the following description, one piezoelectric transducer forms one channel. Each piezoelectric transducer generates an ultrasonic wave in response to the driving signal supplied from a transmission/reception unit 21 (to be described later).

When ultrasonic waves are transmitted to an object P via the ultrasonic probe 11, the transmitted ultrasonic waves (to be referred to as the transmission ultrasonic waves hereinafter) are reflected by a discontinuity surface of acoustic impedance of a living body tissue in the object. The piezoelectric transducers receive the reflected ultrasonic waves and generate an echo signal. The amplitude of this echo signal depends on an acoustic impedance difference on the discontinuity surface as a boundary concerning the reflection of the ultrasonic waves. In addition, the frequency of the echo signal generated when transmission ultrasonic waves are reflected by a moving blood flow, the surface of the cardiac wall, or the like is subjected to a frequency shift depending on the velocity component of the moving body (the blood flow and the surface of the cardiac wall) in the ultrasonic transmission direction due to the Doppler effect.

The ultrasonic probe 11 will be described below as a mechanical four-dimensional probe which executes three-dimensional scanning by swinging a one-dimensional array in a direction perpendicular to the array direction of a plurality of transducers. Note that the ultrasonic probe 11 is not limited to a mechanical four-dimensional probe, and may be a two-dimensional array probe. That is, the ultrasonic probe 11 is a probe which can acquire three-dimensional echo signals.

The matching layer is provided on the ultrasonic wave radiation surface side of the plurality of piezoelectric transducers to improve the efficiency of transmission/reception of ultrasonic waves to/from the object P. The backing member prevents ultrasonic waves from propagating backward from the piezoelectric transducers.

The apparatus main body 13 includes the transmission/reception unit 21, a B-mode processing unit 23, a Doppler processing unit 25, an ultrasonic image generation unit 27, a specifying information generation unit 29, a selection unit 31, a storage unit 33, an image combining unit 35, the interface unit 37, and a control unit (to be referred to as a CPU (Central Processing Unit)) 39.

The transmission/reception unit 21 supplies a driving signal to each of a plurality of piezoelectric transducers of the ultrasonic probe 11 under the control of the CPU 39 (to be described later). The transmission/reception unit 21 generates a reception signal based on the reception echo signal generated by each piezoelectric transducer.

More specifically, the transmission/reception unit 21 includes a pulse generator, transmission delay circuitry, pulser circuitry, a preamplifier, an analog to digital (to be referred to as A/D hereinafter) converter, reception delay circuitry, and an adder (none of which are shown).

The pulse generator repeatedly generates rate pulses for the formation of transmission ultrasonic waves at a predetermined rate frequency fr Hz (period: 1/fr sec). The generated rate pulses are distributed to channel counts and sent to the transmission delay circuitry.

The transmission delay circuitry gives each rate pulse a delay time (to be referred to as a transmission delay time hereinafter) necessary to focus a transmission ultrasonic wave into a beam and determine transmission directivity for each of the plurality of channels. The storage unit 33 (to be described later) stores the transmission direction or transmission delay time of transmission ultrasonic waves (to be referred to as a transmission delay pattern hereinafter). The CPU 39 (to be described later) refers to the transmission delay pattern stored in the storage unit 33 at the time of transmission of ultrasonic waves.

The pulser circuitry applies a voltage pulse (driving signal) to each of the piezoelectric transducers of the ultrasonic probe 11 at the timing based on this rate pulse. With this operation, an ultrasonic beam is transmitted to the object. The preamplifier amplifies the echo signal received from the object P via the ultrasonic probe 11 for each channel. The A/D converter converts each amplified reception echo signal into a digital signal.

The reception delay circuitry gives the reception echo signals converted into the digital signals delay times (to be referred to as reception delay times hereinafter) required to determine reception directivity. The storage unit 33 (to be described later) stores the reception direction or reception delay time of an echo signal (to be referred to as a reception delay pattern hereinafter). The CPU 39 (to be described later) refers to the reception delay pattern in the storage unit 33 at the time of reception of ultrasonic waves.

The adder adds a plurality of echo signals given the delay times. With this addition, the transmission/reception unit 21 generates a reception signal (to be also referred to as an RF (radiofrequency) signal) with a reflection component from a direction corresponding to the reception directivity being enhanced. The transmission directivity and the reception directivity determine the comprehensive directivity of ultrasonic transmission/reception. This comprehensive directivity determines an ultrasonic beam (so-called "ultrasonic scanning line").

The B-mode processing unit 23 generates B-mode data based on the reception signal output from the transmission/reception unit 21. Note that the B-mode processing unit 23 may generate volume data concerning the B mode based on B-mode data. The B-mode processing unit includes an envelope detector and a logarithmic converter (neither of which is shown). The envelope detector executes envelope detection of the reception signal output from the transmission/reception unit 21. The envelope detector outputs the envelope-detected signal to the logarithmic converter (to be described later). The logarithmic converter relatively enhances a weak signal by logarithmically converting the envelope-detected signal. The B-mode processing unit 23 generates a signal value (B-mode data) for each depth on each scanning line based on the signal enhanced by the logarithmic converter.

The B-mode processing unit 23 may generate volume data based on a plurality of signal values respectively arranged in the azimuth direction, the elevation direction, and the depth direction (to be referred to as the range direction hereinafter) in a scanned region. The range direction is the depth direction on a scanning line. The azimuth direction is, for example, an electronic scanning direction along the array direction of one-dimensional ultrasonic transducers. The elevation direction is the mechanical swinging direction of the one-dimensional ultrasonic transducers. Note that volume data may be data obtained by arranging a plurality of pixel values, a plurality of luminance values, or the like in the azimuth direction, the elevation direction, and the range direction, respectively, along scanning lines.

The Doppler processing unit 25 generates Doppler data based on the reception signal output from the transmission/reception unit 21. Note that the Doppler processing unit 25 may generate volume data concerning the Doppler mode based on Doppler data. The Doppler processing unit 25 includes a mixer, a low pass filter (to be referred to an LPF hereinafter), and a velocity/variance/power computation device (none of which are shown). The mixer multiplies the reception signal output from the transmission/reception unit 21 by a reference signal having a frequency f0 equal to the transmission frequency. This multiplication obtains a signal having a component with a Doppler shift frequency fd and a signal having a frequency component of (2f0+fd). The LPF removes a signal of a high-frequency component (2f0+fd) from a signal having two types of frequency components from the mixer. The Doppler processing unit 25 generates a Doppler signal having the component with the Doppler shift frequency fd by removing the signal of the high-frequency component (2f0+fd).

Note that the Doppler processing unit 25 may use a quadrature detection scheme to generate Doppler signals. In this case, the Doppler processing unit performs quadrature detection to convert a reception signal (RF signal) into an IQ signal. The Doppler processing unit 25 generates a Doppler signal having the Doppler shift frequency fd by performing complex Fourier transform on the IQ signal. Doppler signals are, for example, Doppler components based on a blood flow, tissue, and contrast medium.

The velocity/variance/power computation device includes an MTI (Moving Target Indicator) filter, an LPF filter, and an autocorrelation computation unit (none of which are shown). Note that this device may include a cross-correlation computation unit instead of an autocorrelation computation unit. The MTI filter removes a Doppler component (a clutter component) caused by the respiratory movement or pulsatory movement of an organ or the like from a generated Doppler signal. The MTI filter is used to extract a Doppler component (to be referred to as a blood flow Doppler component hereinafter) concerning a blood flow from a Doppler signal. The LPF is used to extract a Doppler component (to be referred to as a tissue Doppler component hereinafter) concerning the movement of the tissue from a Doppler signal.

The autocorrelation computation unit calculates autocorrelation values concerning a blood flow Doppler signal and a tissue Doppler component. The autocorrelation computation unit calculates the average velocity values of the blood flow and the tissue, variances, the reflection intensities (powers) of Doppler signals, and the like based on the calculated autocorrelation values. The velocity/variance/power computation device generates color Doppler data at the respective positions in a scanned region based on the average velocity values of the blood flow and the tissue, the variances, the reflection intensities of the Doppler signals, and the like based on a plurality of Doppler signals. Doppler signals and color Doppler data will be collectively referred to as Doppler data hereinafter.

The ultrasonic image generation unit 27 includes a digital scan converter (to be referred to as a DSC hereinafter) (not shown) and an image memory (neither of which is shown). The ultrasonic image generation unit 27 executes coordinate transformation processing (resampling) for the DSC. Coordinate transformation processing is to transform, for example, a scanning line signal string for ultrasonic scanning, which is formed from B-mode data and Doppler data, into a scanning line signal string in a general video format typified by a TV format. The ultrasonic image generation unit 27 generates an ultrasonic image as a display image by executing coordinate transformation processing. More specifically, the ultrasonic image generation unit 27 generates a B-mode image based on B-mode data. The ultrasonic image generation unit 27 generates a color blood flow image such as an average velocity image or variance image, a power blood flow image indicating the reflection intensity of a Doppler signal, and the like based on color Doppler data.

The ultrasonic image generation unit 27 generates a superimposed image by superimposing a color blood flow image on a B-mode image. The ultrasonic image generation unit 27 generates a superimposed image by superimposing a power blood flow image on a B-mode image. For the sake of easy explanation, assume that the superimposed image obtained by superimposing a color blood flow image on a B-mode image and the superimposed image obtained by superimposing a power blood flow image on a B-mode image will be collectively referred to as color Doppler images hereinafter. The ultrasonic image generation unit 27 generates a Doppler waveform image indicating a Doppler waveform based on a Doppler signal. The ultrasonic image generation unit 27 generates an ultrasonic image having a color Doppler image and a Doppler waveform image. Note that an ultrasonic image may have a B-mode image and a Doppler waveform image.

The ultrasonic image generation unit 27 generates a series of a plurality of ultrasonic images along a time series until a predetermined operation concerning the acquisition of Doppler waveforms is executed via the input unit 17 (to be described later). Note that the ultrasonic image generation unit 27 can also generate a series of ultrasonic images again after the acquisition of Doppler waveforms. The ultrasonic image generation unit 27 outputs the generated ultrasonic images to the image combining unit 35 (to be described later) and an image memory (not shown).

The image memory stores data (to be referred to as image data hereinafter) corresponding to the generated ultrasonic images. The image data stored in the image memory are read out in accordance with the instruction issued by the operator via the input unit 17 (to be described later). The image memory is a memory which saves, for example, ultrasonic images corresponding to a series of frames immediately before freezing. Continuously displaying (cine displaying) the images stored in the image memory on the display unit 15 can display a moving ultrasonic image on the display unit 15. The image memory may store a plurality of ultrasonic images included in a predetermined time width range centered on the time corresponding the color Doppler image selected by the selection unit 31 (to be described later). With this operation, continuously displaying (cine displaying) a plurality of ultrasonic images included in the predetermined time width range will display a moving ultrasonic image on the display unit 15.

The specifying information generation unit 29 generates predetermined specifying information concerning a color Doppler image suitable for recording based on ultrasonic images. Predetermined specifying information is, for example, at least one of the following pieces of information: information (to be referred to as color image information hereinafter) concerning a color blood flow image and a power blood flow image, information (to be referred to as B-mode image information hereinafter) concerning a B-mode image, information (to be referred to as blood flow velocity information hereinafter) concerning a blood flow velocity on a Doppler waveform image, and information (biological information) concerning a periodic biological signal waveform corresponding to a Doppler waveform. A biological signal waveform includes, for example, a Doppler waveform such as an electrocardiographic waveform, phonocardiographic waveform, or sphygmographic waveform and a periodic waveform associated with the generation of a color Doppler image. For the sake of easy explanation, assume that a biological signal waveform is an electrocardiographic waveform.

More specifically, the specifying information generation unit 29 counts the numbers of pixels (to be referred to as the numbers of color pixels hereinafter) in color regions of color blood flow images and power blood flow images, as color image information, concerning a series of ultrasonic images. The specifying information generation unit 29 outputs the generated color image information (the numbers of color pixels) to the selection unit 31 (to be described later).

The specifying information generation unit 29 generates a difference absolute value image representing the absolute values of differences between two temporally adjacent B-mode images on a series of ultrasonic images. The specifying information generation unit 29 detects the motion of a B-mode image in a scanned region by using the difference absolute value image. The motion of the B-mode image is, for example, a motion vector at each point in the scanned region. That is, the specifying information generation unit 29 generates a motion vector field indicating motion vectors at the respective points in the scanned region. Note that the specifying information generation unit 29 may detect motion vectors by correlation matching using two temporally adjacent B-mode images. With these operations, the specifying information generation unit 29 generates, as B-mode image information, a motion vector field corresponding to each of a series of ultrasonic images. The specifying information generation unit 29 outputs the generated B-mode image information (motion vector field) to the selection unit 31 (to be described later).

The specifying information generation unit 29 determines, as blood flow velocity information, a maximum flow velocity time corresponding to a maximum flow velocity value based on the Doppler waveform on a Doppler waveform image. More specifically, the specifying information generation unit 29 specifies the maximum flow velocity value of a blood flow based on the Doppler waveform. The specifying information generation unit 29 determines a maximum flow velocity time based on the specified maximum flow velocity value. The specifying information generation unit 29 outputs the determined maximum flow velocity time to the selection unit 31 (to be described later). Note that the specifying information generation unit 29 may generate, as blood flow velocity information, average flow velocity values of a blood flow near the sample gates set on the color blood flow images on a series of ultrasonic images with respect to each of the series of ultrasonic images.

The specifying information generation unit 29 determines the set time of a measurement cursor (to be referred to as the measurement cursor set time hereinafter) based on the position of the measurement cursor set on the Doppler waveform on a Doppler waveform image. The measurement cursor is a cursor for setting, via the input unit 17, a position to measure a blood flow velocity on the Doppler waveform on the Doppler waveform image displayed on the display unit 15. That is, a blood flow velocity is measured at the time corresponding to the position set on the Doppler waveform.

FIG. 2 is a view showing an example of the list of specifying information generated by the specifying information generation unit 29. Note that the specifying information generation unit 29 may generate at least one piece of specifying information concerning the plurality of items shown in FIG. 2.

The selection unit 31 selects a color Doppler image suitable for recording from a plurality of color Doppler images on a series of ultrasonic images based on specifying information in response to a predetermined operation via the input unit 17 (to be described later). The selection unit 31 outputs the selected color Doppler image to the display unit 15 and the storage unit 33. The predetermined operation is, for example, an input operation via the input unit 17, such as the operation of updating a Doppler waveform or a freezing operation. Note that the predetermined operation may be pressing of a Doppler mode start button corresponding to an execution instruction concerning pulse Doppler processing or continuous wave Doppler processing.

More specifically, the selection unit 31 selects a color Doppler image having the maximum number of color pixels or the maximum average flow velocity value as a color Doppler image suitable for recording from a series of ultrasonic images. Note that the selection unit 31 may select a color Doppler image having a B-mode image with the minimum motion vector field from a series of ultrasonic images. Note that a series of ultrasonic images as selection targets may be all the ultrasonic images generated concerning the object. Alternatively, a series of ultrasonic images as selection targets may be a plurality of ultrasonic images within the range set in advance by a predetermined phase on an electrocardiographic waveform.

In addition, when triplex display is executed, that is, the superimposed image obtained by superimposing a color blood flow image on a B-mode image and a Doppler waveform image are simultaneously displayed, it is possible to select a color Doppler image corresponding to the maximum flow velocity time from a series of ultrasonic images. Note that when triplex display is not performed, the selection unit 31 can also select a color Doppler image corresponding to the maximum flow velocity time from a series of ultrasonic images based on the time interval from the time of an R-wave of an electrocardiographic waveform immediately before the maximum flow velocity time to the maximum flow velocity time and the time of the R-wave immediately before the maximum flow velocity time.

FIG. 3 is a view showing the maximum flow velocity time, the time of an R-wave immediately before the maximum flow velocity time, and the time interval when triplex display is not performed, that is, a Doppler waveform image and an electrocardiographic waveform are displayed. Note that referring to FIG. 3, a B-mode image may be simultaneously displayed. As shown in FIG. 3, assume that triplex display is not performed. In this case, when the maximum flow velocity time is determined, the selection unit 31 selects a color Doppler image corresponding to the maximum flow velocity time from a series of ultrasonic images based on the time of an R-wave immediately before the maximum flow velocity time and the time interval.

The selection unit 31 determines the time interval between the time of an R-wave immediately before the measurement cursor set time and the measurement cursor set time. Note that if a biological signal waveform is a phonocardiographic waveform, the selection unit 31 may determine the time interval between the time of the I sound of a phonocardiographic waveform and the measurement cursor set time. If a biological signal waveform is a sphygmographic waveform, the selection unit 31 may determine the time interval between the time of the a-wave of the acceleration sphygmographic wave of a sphygmographic waveform and the measurement cursor set time. The selection unit 31 can select a color Doppler image corresponding to the measurement cursor set time from a series of ultrasonic images based on the determined time interval and the time of the R-wave.

FIG. 4 is a view showing the measurement cursor set time, the time of the R-wave, and the time interval on an electrocardiogram displayed together with triplex display. As shown in FIG. 4, upon setting a measurement cursor in triplex display, the selection unit 31 selects a color Doppler image corresponding the measurement cursor set time from a series of ultrasonic images based on the time of the R-wave immediately before the measurement cursor set time and the time interval.

Note that the selection unit 31 can also select a plurality of electrocardiographic phases corresponding to the measurement cursor set time on an electrocardiographic waveform. At this time, the selection unit 31 selects a plurality of color Doppler images respectively corresponding to a plurality of electrocardiographic phases from a series of ultrasonic images. The selection unit 31 may then select, as a color Doppler image suitable for recording, a color Doppler image having, for example, the maximum number of color pixels, the maximum average flow velocity value, or the minimum motion vector field from the plurality of selected color Doppler images.

The selection unit 31 can also select a color Doppler image suitable for recording from a series of ultrasonic images by using, for example, a combination of a plurality of specifying information items like those shown in FIG. 2, that is, "number of color pixels", "average flow velocity value", "intensity", "motion vector field", "maximum flow velocity time", "biological signal waveform", and "measurement cursor set time".

The storage unit 33 stores various types of data groups such as a plurality of reception delay patterns with different focus depths, a plurality of transmission delay patterns, diagnosis protocols, and transmission/reception conditions. The storage unit 33 stores the ultrasonic images, B-mode images, color Doppler images, color blood flow images, power blood flow images, Doppler waveform images, and the like which are generated by the ultrasonic image generation unit 27. The storage unit 33 stores a control program for the ultrasonic diagnostic apparatus 1, a specifying information generation program concerning the generation of specifying information, an image selection program for selecting a color Doppler image suitable for recording, and the like. The storage unit 33 stores the color Doppler image selected by the selection unit 31.

The image combining unit 35 combines various types of parameters, character information, scale marks, and the like with B-mode images, color Doppler images, Doppler waveform images, and the like. The image combining unit 35 outputs the B-mode images, the Doppler images, the color Doppler images, the Doppler waveform images, and the like which are combined with various parameters, character information, scale marks, and the like to the display unit 15.

The interface unit 37 is an interface associated with the input unit 17, a network, an external storage device (not shown), and the biological signal measurement unit 19. Data such as the ultrasonic images, the analysis results, and the like, which are obtained by the apparatus main body 13, can be transferred to other apparatuses via the interface unit 37 and the network. Note that the interface unit 37 can also download, via the network, medical images concerning objects acquired by other medical image diagnostic apparatuses (not shown). In addition, the biological signal measurement unit 19 typified by an electrocardiograph, a phonocardiograph, sphygmograph, or the like is connected to the interface unit 37.

The CPU 39 reads out the transmission delay pattern, the reception delay pattern, and the operation control program in the storage unit 33 based on the frame rate, the scan depth, and transmission start/end which are input by the operator via the input unit 17, and controls the apparatus main body 13 in accordance with the readout information. The CPU 39 reads out the specifying information generation program from the storage unit 33, and controls the specifying information generation unit 29. The CPU 39 reads out the image selection program from the storage unit 33, and controls the selection unit 31.

The display unit 15 displays a B-mode image, color Doppler image, Doppler waveform image, biological signal waveform, or the like based on an output from the image combining unit 35. Note that the display unit 15 may execute adjustment such as brightness correction, contrast correction, dynamic range correction, and γ correction and color mapping with respect to a displayed image. The display unit 15 executes triplet display to display a color Doppler image together with a Doppler waveform image. The display unit 15 displays the color Doppler image selected by the selection unit 31. Note that the display unit 15 can display a moving ultrasonic image by continuously displaying (cine displaying) a plurality of ultrasonic images included in a predetermined time width range.

FIG. 5 is a view showing a selected color Doppler image together with a Doppler waveform image. As shown in FIG. 5, the display unit 15 displays the color Doppler image selected by the selection unit 31.

The input unit 17 is connected to the interface unit 37 to input, to the apparatus main body 13, various types of instructions, commands, information, selections, and settings from the operator. The input unit 17 includes input devices such as a trackball, switch buttons, a mouse, and a keyboard (none of which are shown). The input device detects the coordinates of the cursor displayed on the display screen and outputs the detected coordinates to the CPU 39 (to be described later). Note that the input device may be a touch command screen provided to cover the display screen. In this case, the input unit 17 detects touched and designated coordinates by a coordinate reading principle such as an electromagnetic induction scheme, magnetostriction scheme, or a pressure-sensitive scheme, and outputs the detected coordinates to the CPU 39. When, for example, the operator operates the end button of the input unit 17, the ultrasonic transmission/reception is terminated, and the apparatus main body 13 is set in a pause state.

In addition, the input unit 17 inputs a predetermined operation such as the operation of updating a Doppler waveform, a freezing operation, or the pressing of the Doppler mode start button to the apparatus main body 13. The apparatus main body 13 executes transmission/reception of ultrasonic waves to/from an object to acquire a Doppler waveform in response to the input of the operation of updating a Doppler waveform or the pressing of the Doppler mode start button. In addition, the input unit 17 can arbitrarily select/input items, of a plurality of specifying information items, which are used to select a color Doppler image in accordance with an instruction from the operator.

(Color Doppler Image Selection Function)

The color Doppler image selection function is a function of selecting a color Doppler image suitable for recording from a series of ultrasonic images based on specifying information. The processing associated with the color Doppler image selection function (to be referred to as the color Doppler image selection processing hereinafter) will be described below.

FIG. 6 is a flowchart showing an example of a procedure for color Doppler image selection processing.

An ultrasonic image is generated by transmitting/receiving ultrasonic waves to/from an object (step Sa1). Specifying information is generated based on the generated ultrasonic image (step Sa2). The storage unit 33 stores the generated specifying information in correspondence with a color Doppler image on the ultrasonic image (step Sa3). The processing in steps Sa2 and Sa3 is repeated until a predetermined operation is input (step Sa4).

When a predetermined operation is input (step Sa4), a color Doppler image suitable for recording is selected based on the specifying information (step Sa5). The display unit 15 displays the selected color Doppler image (step Sa6). The storage unit 33 stores the selected color Doppler image (step Sa7).

(First Modification)

A difference from the first embodiment is that the above motion amount of B-mode image information is detected by the differences between three or more temporally adjacent B-mode images. That is, this modification is configured to detect motion vectors by, for example, calculating the differences between n (n is a natural number equal to or more than 3) chronologically continuous B-mode images.

The specifying information generation unit 29 generates a difference absolute value image indicating the absolute values of differences between two adjacent B-mode images of three or more temporally adjacent B-mode images on a series of ultrasonic images. When, for example, n (n is a natural number equal to or more than 3) chronologically continuous B-mode images are to be used, (n−1) difference absolute value images are generated. The specifying information generation unit 29 generates a motion vector field indicating a motion vector at each point in a scanned region by using (n−1) difference absolute value images. Note that the specifying information generation unit 29 may detect motion vectors by correlation matching using at least three or more temporally adjacent B-mode images. With these operations, the specifying information generation unit 29 generates a motion vector field corresponding to each of a series of ultrasonic images as B-mode image information. The specifying information generation unit 29 outputs the generated B-mode image information (motion vector field) to the selection unit 31.

(Second Modification)

A difference from the first embodiment is that specifying information is generated based on each of a series of ultrasonic images after the input of a predetermined operation, and a color Doppler image is selected from the series of ultrasonic images based on the generated specifying information.

The image memory or the storage unit 33 temporarily stores a series of ultrasonic images.

Upon receiving a predetermined operation via the input unit 17, the specifying information generation unit 29 generates specifying information based on the series of generated ultrasonic images. Note that the specifying information generation unit 29 may generate specifying information with respect to each of a series of ultrasonic images belonging to a predetermined time width (e.g., one cardiac period) including the input time of a predetermined operation.

Figure 10:
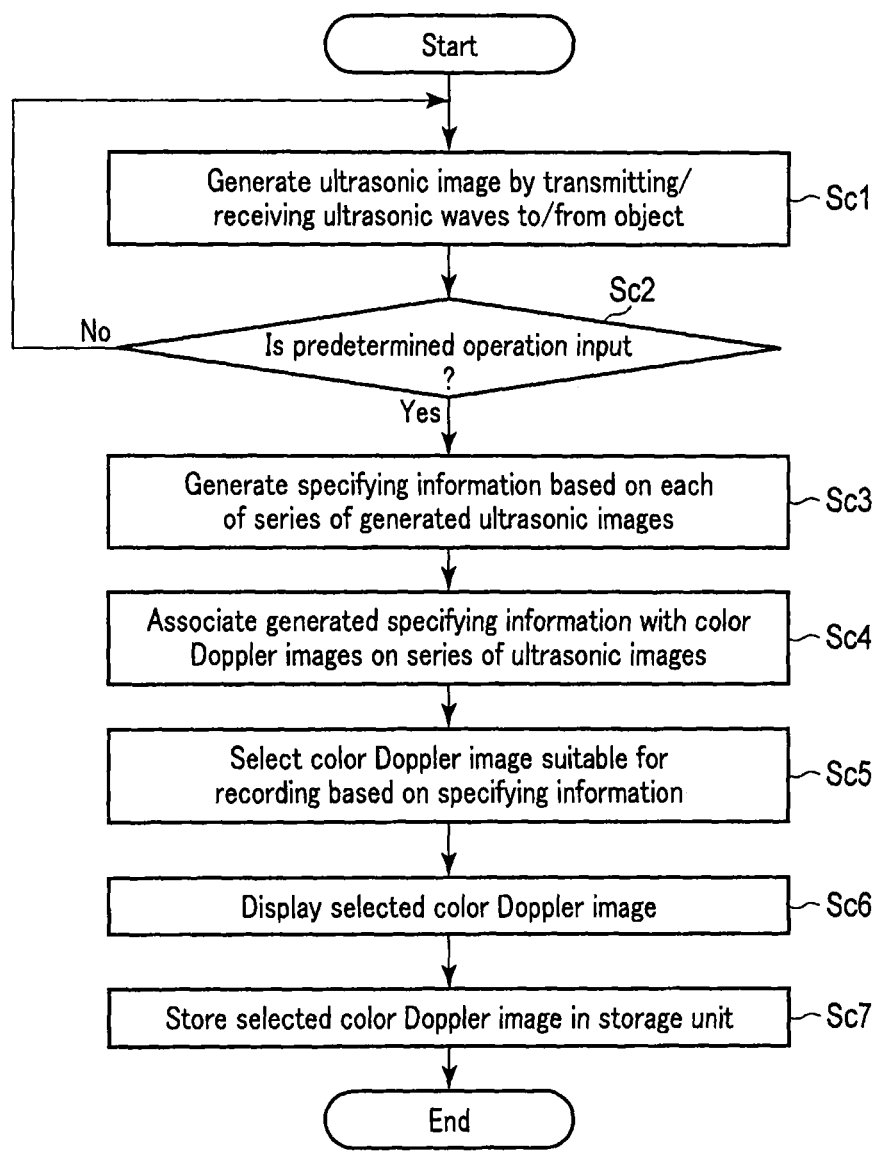
FIG. 10 is a flowchart showing an example of a procedure for color Doppler image selection processing according to the second modification of the first embodiment.

FIG. 10 is a flowchart showing an example of a procedure for color Doppler image selection processing according to this modification.

A series of ultrasonic images are generated along a time series by transmitting/receiving ultrasonic waves to/from an object (step Sc1). The storage unit 33 or the image memory temporarily stores the series of generated ultrasonic images. When a predetermined operation is input via the input unit 17 (step Sc2), specifying information is generated based on each of the series of generated ultrasonic images (step Sc3). The generated specifying information is associated with color Doppler images on the series of ultrasonic images (step Sc4). A color Doppler image suitable for recording is selected based on the specifying information (step Sc5). The display unit 15 displays the selected color Doppler image (step Sc6). The storage unit 33 stores the selected color Doppler image (step Sc7).

(Third Modification)

A difference from the first embodiment is that a series of ultrasonic images in a predetermined time width including the input time of a predetermined operation are displayed in the form of a list after the input of the predetermined operation, and a color Doppler image is selected in accordance with the input of a selection instruction from the operator.

When a predetermined operation is input via the input unit 17, the display unit 15 displays a series of ultrasonic images in a predetermined time width including the input time of the predetermined operation in the form of a list. The predetermined time width is, for example, a time width concerning a predetermined number of frames set in advance. Alternatively, the predetermined time width may be a predetermined time width range centered on the input time. The predetermined range is, for example, a time corresponding to a predetermined number of frames.

Note that the display unit 15 may display a series of ultrasonic images in a predetermined time width in the form of a list, together with specifying information corresponding to each image. The display unit 15 may also display a plurality of thumbnail images respectively corresponding to a series of ultrasonic images in a predetermined time width in the form of a list. In addition, the display unit 15 may continuously display a series of ultrasonic images in a predetermined time width as a moving image.

The input unit 17 inputs the selection instruction issued by the operator with respect to a series of ultrasonic images displayed in the form of a list, thumbnail images, or a moving ultrasonic image in a predetermined time width.

The selection unit 31 selects the image selected by the selection instruction from the series of ultrasonic images.

Figure 11:
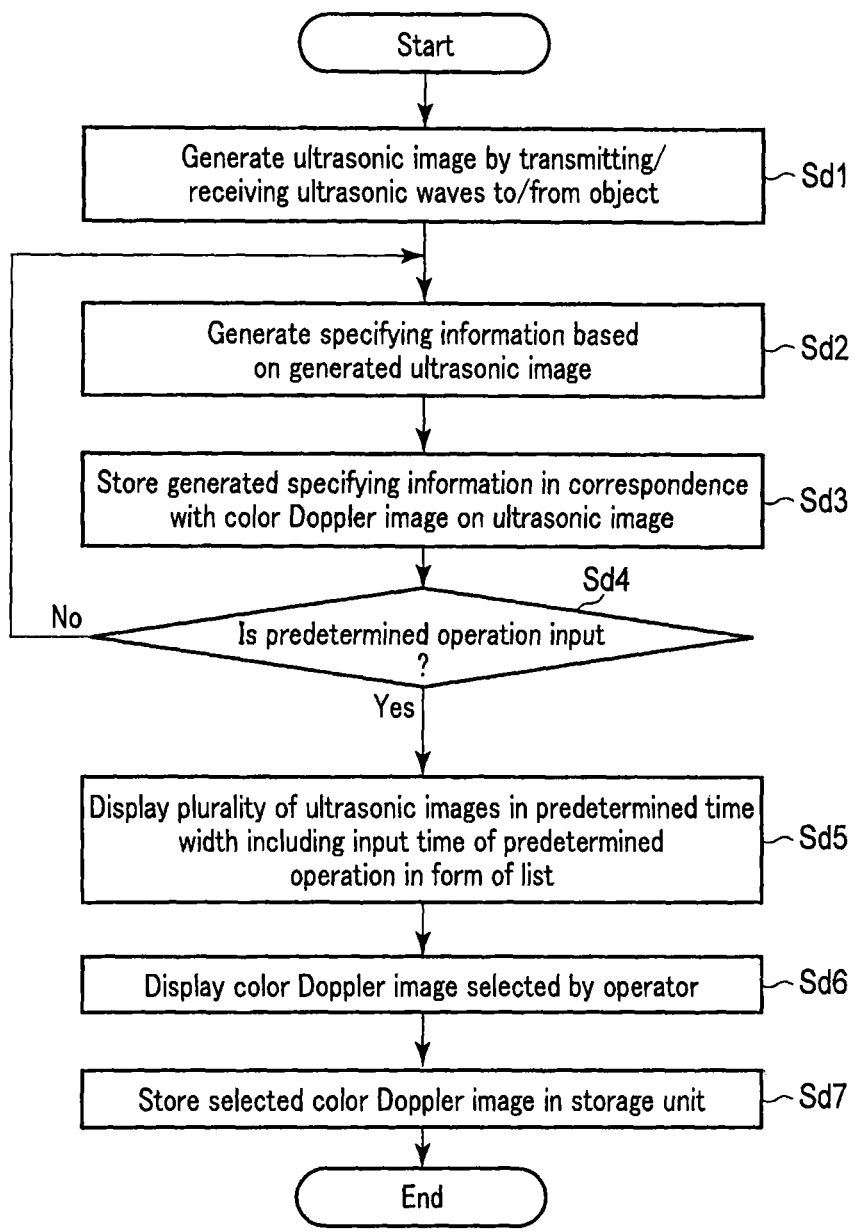
FIG. 11 is a flowchart showing an example of a procedure for color Doppler image selection processing according to the third modification of the first embodiment.

FIG. 11 is a flowchart showing an example of a procedure for color Doppler image selection processing according to this modification.

A series of ultrasonic images are generated along a time series by transmitting/receiving ultrasonic waves to/from an object (step Sd1). Specifying information is generated based on each of the series of generated ultrasonic images (step Sd2). The generated specifying information is stored in correspondence with the color Doppler images on the series of ultrasonic images (step Sd3). When a predetermined operation is input via the input unit 17 (step Sd4), a series of ultrasonic images included in a predetermined time width including the input time of the predetermined input operation are displayed in the form of a list (step Sd5). The color Doppler image selected by the operator from the series of ultrasonic images displayed in the form of a list is displayed (step Sd6). The storage unit 33 stores the selected color Doppler image (step Sd7).

According to the above arrangement, the following effects can be obtained.

The ultrasonic diagnostic apparatus 1 according to this embodiment can select a color Doppler image optimal for recording based on the specifying information generated based on ultrasonic images. This makes it possible to display and store a color Doppler image (a color Doppler image having high image quality, the maximum number of color pixels, the maximum flow velocity value, and the like) optimal for recording which is desired by the operator. As described above, it is possible to prevent a color Doppler image from being influenced by the respiration and pulsation of an object, the shaking of the hand of the operator who holds the ultrasonic probe, and the like depending on the execution timing of a predetermined operation. In addition, according to this embodiment, since a color Doppler image optimal for recording can be automatically selected, it is possible to improve examination efficiency without bothering the operator. Furthermore, it is possible to avoid the storage of a color Doppler image in a state unsuitable for recording.

In addition, according to the first modification, B-mode image information (motion vector field) of specifying information can be generated by using three or more B-mode images.

According to the second modification, it is possible to generate specifying information after a predetermined operation and select a color Doppler image. This makes it possible to automatically select a color Doppler image optimal for recording after a predetermined operation without bothering the operator, thereby improving examination efficiency.

In addition, according to the third modification, a series of ultrasonic images in a predetermined time width including the input time of a predetermined operation are displayed in the form of a list after the predetermined operation. This makes it possible to store the color Doppler image selected in accordance with a selection instruction from the operator. This can given the operator the right to select a color Doppler image from a series of ultrasonic images near the input time of the predetermined operation. According to this modification, therefore, it is possible to prevent the selection of a color Doppler image which is not intended by the operator.

Second Embodiment

A difference from the first embodiment is that indices are generated based on specifying information, and a color Doppler image suitable for recording is selected based on the generated indices.

Figure 7:
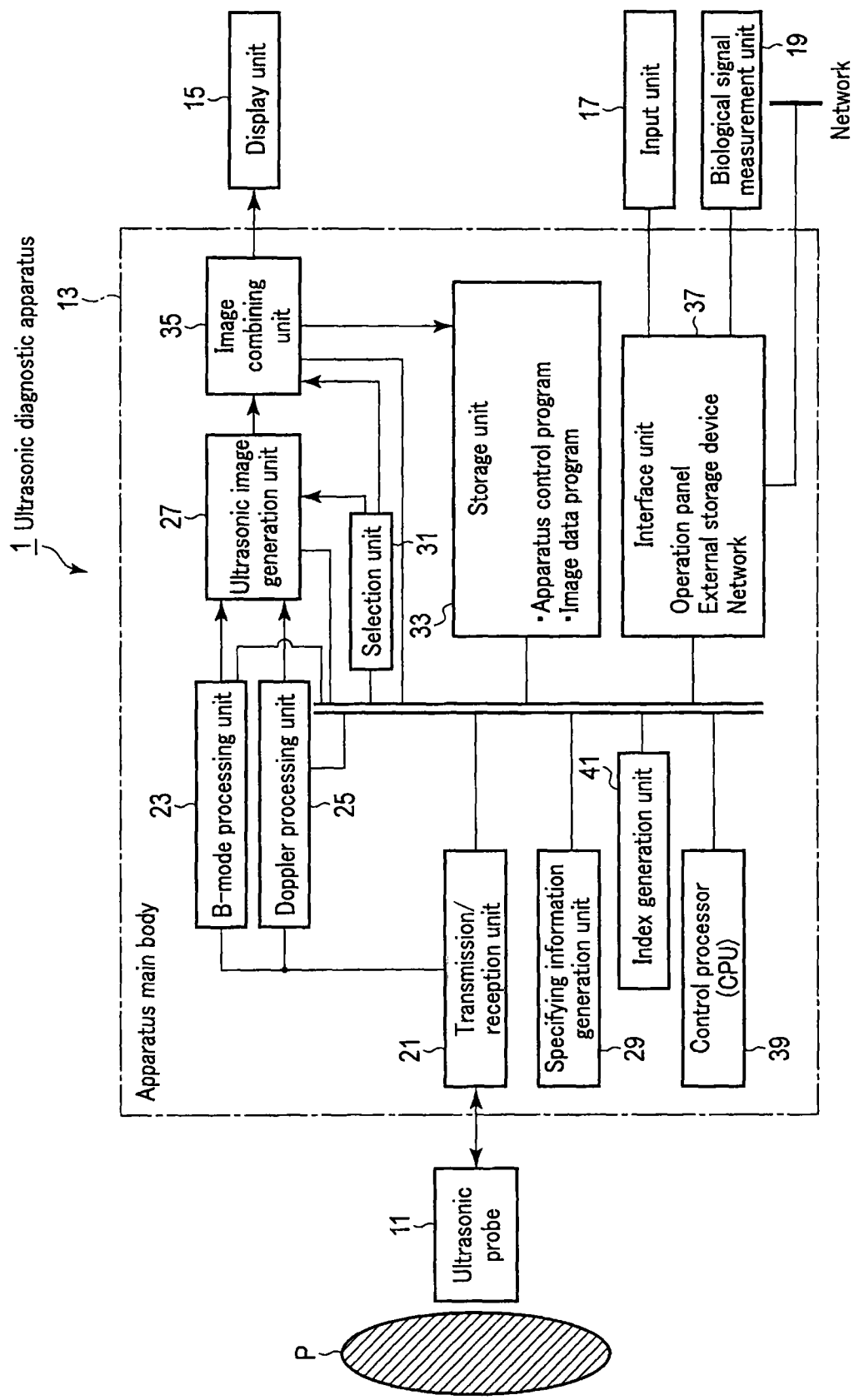
FIG. 7 is a block diagram showing the arrangement of an ultrasonic diagnostic apparatus according to the second embodiment.

FIG. 7 is a block diagram showing the arrangement of an ultrasonic diagnostic apparatus according to the second embodiment.

An index generation unit 41 generates indices concerning a color Doppler image suitable for recording in correspondence with each of a series of ultrasonic images based on specifying information. More specifically, the index generation unit 41 generates indices (to be referred to as color indices hereinafter) concerning color image information based on the numbers of color pixels and the brightness intensities of power blood flow images. Color indices are indices concerning the sufficient amounts of blood flows in the display regions of a color blood flow image and a power blood flow image. That is, the magnitude of a color index is proportional to the abundance of a blood flow.

The index generation unit 41 generates indices concerning motion vectors (to be referred to as motion indices hereinafter) in a scanned region based on two temporally adjacent B-mode images. A motion index is an index concerning the blur of a B-mode image. That is, the magnitude of a motion index is proportional to the motion of a scanned region.

The index generation unit 41 generates an index concerning blood flow velocity information (to be referred to as a blood flow velocity index hereinafter) based on an average flow velocity value near a sample gate (to be referred to as a sample gate neighboring region hereinafter) on a color blood flow image and the maximum flow velocity value on a Doppler waveform. A blood flow velocity index is an index concerning a blood flow velocity in a sample gate neighboring region including a sample gate. That is, the magnitude of a blood flow velocity index is proportional to the velocity of a blood flow.

The index generation unit 41 generates the plurality of indices described above in correspondence with a series of ultrasonic images. The index generation unit 41 outputs the plurality of generated indices to a storage unit 33 and a selection unit 31.

The storage unit 33 stores the plurality of indices described above in correspondence with each of the series of ultrasonic images.

The selection unit 31 selects a color Doppler image suitable for recording from the series of ultrasonic images based on at least one of a color index, a motion index, and a blood flow velocity index. For the sake of easy explanation, assume that the indices used by the selection of a color Doppler image are color indices, motion indices, and blood flow velocity indices. When a predetermined operation is input via an input unit 17, the selection unit 31 selects a plurality of color Doppler images having large color indices from a series of ultrasonic images. The selection unit 31 then selects a plurality of color Doppler images with small motion indices from the plurality of color Doppler images selected by using the color indices. Lastly, the selection unit 31 selects a color Doppler image with the maximum blood flow velocity index from the plurality of color Doppler images selected by using the motion indices. The selection unit 31 outputs the color Doppler image selected by these indices to the storage unit 33 and a display unit 15.

The input unit 17 can selectively input, as needed, indices of a plurality of indices which are generated and indices used for the selection of a color Doppler image in accordance with an instruction from the operator.

(Color Doppler Image Index Selection Function)

The color Doppler image index selection function is a function of selecting a color Doppler image suitable for recording from a series of ultrasonic images by using the indices generated based on specifying information. The processing associated with the color Doppler image index selection function (to be referred to as the color Doppler image index selection processing hereinafter) will be described below.

Figure 8:
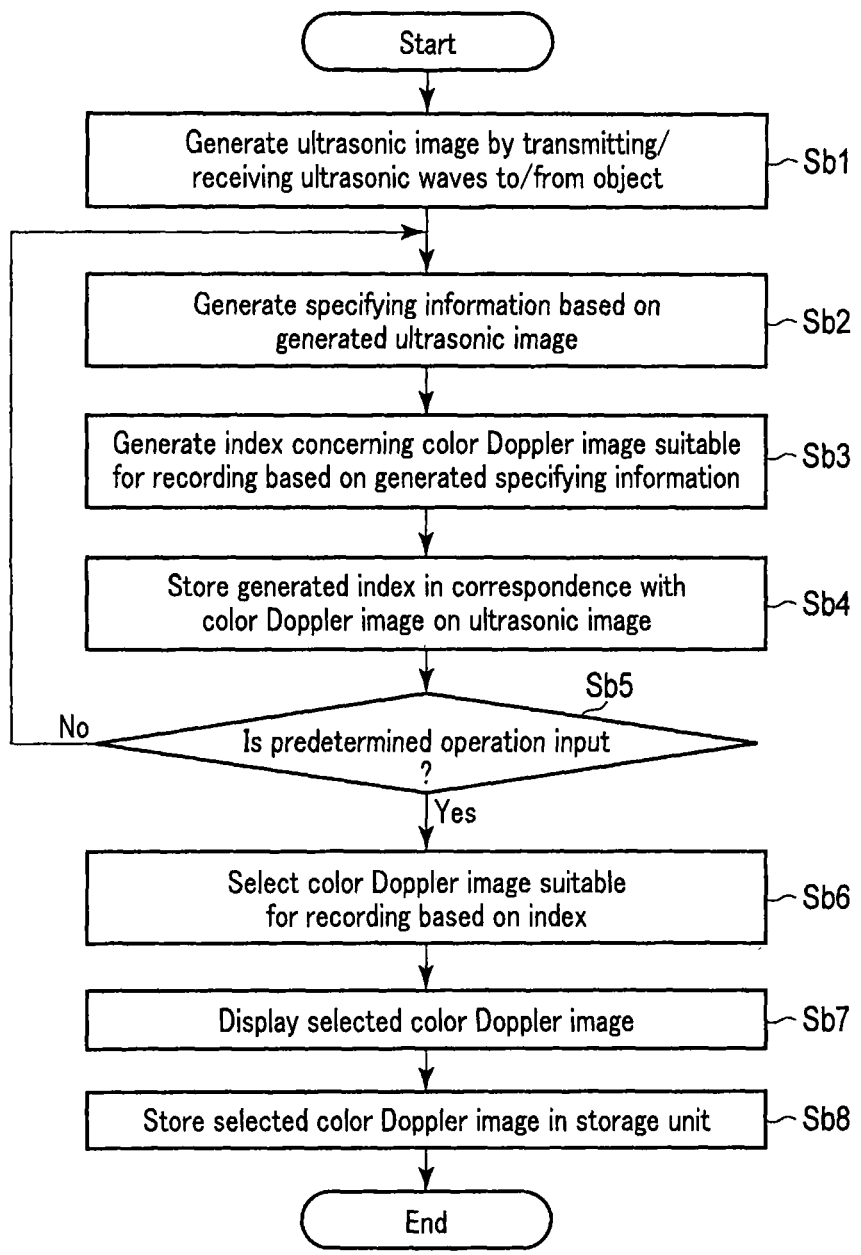
FIG. 8 is a flowchart showing an example of a procedure for color Doppler image index selection processing.
Figure 9:
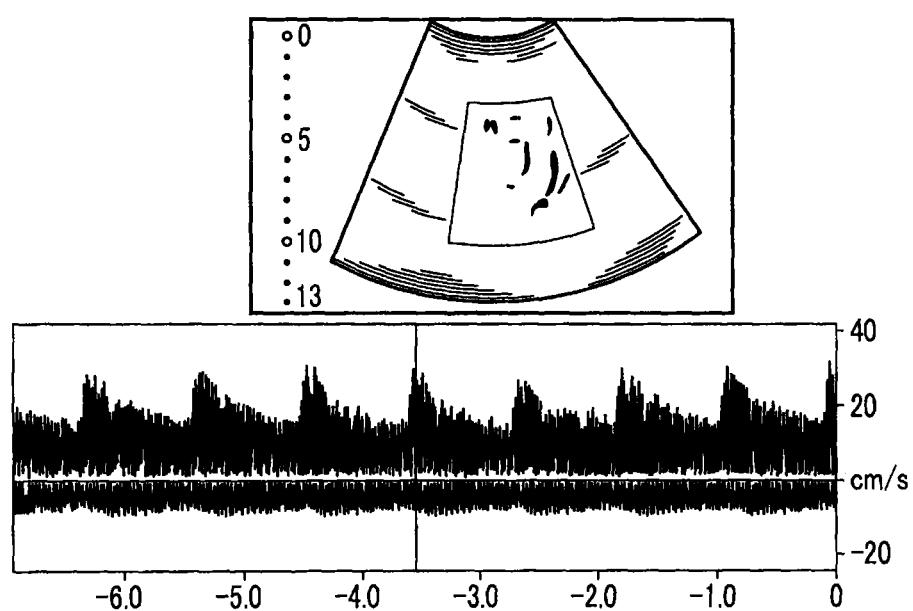
FIG. 9 is a view showing an example of a color Doppler image which is not optimal for recording according to a related art.

FIG. 8 is a flowchart showing an example of a procedure for color Doppler image index selection processing.

Ultrasonic images are generated by transmitting/receiving ultrasonic waves to/from an object (step Sb1). Specifying information is generated based on the generated ultrasonic images (step Sb2). The indices associated with a color Doppler image suitable for recording are generated based on the generated specifying information in correspondence with each of a series of ultrasonic images (step Sb3). The storage unit 33 stores the generated indices together with the color Doppler image on the ultrasonic image in correspondence with the color Doppler image (step Sb4). The processing from step Sb2 to step Sb4 is repeated until a predetermined operation is input (step Sb5).

When the predetermined operation is input (step Sb5), a color Doppler image suitable for recording is selected based on the indices (step Sb6). The display unit 15 displays the selected color Doppler image (step Sb7). The storage unit 33 stores the selected color Doppler image (step Sb8).

According to the above arrangement, the following effects can be obtained.

An ultrasonic diagnostic apparatus 1 according to this embodiment generates a plurality of indices based on the specifying information generated based on ultrasonic images. A color Doppler image optimal for recording can be selected based on the generated indices. This makes it possible to display and store a color Doppler image (a color Doppler image having high image quality, the maximum number of color pixels, the maximum flow velocity value, and the like) optimal for recording which is desired by the operator. As described above, it is possible to prevent a color Doppler image from being influenced by the respiration and pulsation of an object, the shaking of the hand of the operator who holds the ultrasonic probe, and the like depending on the execution timing of a predetermined operation. In addition, according to this embodiment, since a color Doppler image optimal for recording can be automatically selected, it is possible to improve examination efficiency without bothering the operator. Furthermore, it is possible to avoid the storage of a color Doppler image in a state unsuitable for recording.

In addition, each function according to the embodiments can be implemented by installing programs for executing the above processing in a computer such as a workstation and loading them in the memory. In this case, the programs which can cause the computer to execute the above method can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus, comprising:
   transmission/reception circuitry configured to transmit/receive an ultrasonic wave to/from an object via a piezoelectric transducer;
   ultrasonic image generation circuitry configured to generate a series of color Doppler images along a time series based on an output from the transmission/reception circuitry and generate a Doppler waveform image based on an output from the transmission/reception circuitry;
   specifying information generation circuitry configured to generate a maximum flow velocity time corresponding to a maximum flow velocity value in a Doppler waveform on the Doppler waveform image;
   selection circuitry configured to select a color Doppler image corresponding to the maximum flow velocity time from the series of color Doppler images based on generation of the maximum flow velocity time in response to a predetermined operation executed after generation of the Doppler waveform image; and
   storage circuitry configured to store the selected color Doppler image in response to the predetermined operation.

2. The ultrasonic diagnostic apparatus according to claim 1, wherein
   the specifying information generation circuitry is further configured to generate a periodic electrocardiographic waveform corresponding to the Doppler waveform, and
   the selection circuitry is further configured to select the color Doppler image corresponding to the maximum flow velocity time based on a time interval from a time of an R-wave of the electrocardiographic waveform immediately before the maximum flow velocity time and the time of the R-wave immediately before the maximum flow velocity time in response to the predetermined operation.

3. The ultrasonic diagnostic apparatus according to claim 2, wherein the specifying information generation circuitry is further configured to generate a measurement cursor set time corresponding to a position of a measurement cursor set on the Doppler waveform, and
   the selection circuitry is further configured to select the color Doppler image based on the measurement cursor set time and the time of the R-wave of the electrocardiographic waveform.

4. The ultrasonic diagnostic apparatus according to claim 1, wherein the predetermined operation includes a freezing operation.

5. The ultrasonic diagnostic apparatus according to claim 1, further comprising index generation circuitry configured to generate an index concerning the color Doppler image in correspondence with each of the series of color Doppler images based on the specifying information including the maximum flow velocity time,
   wherein the selection circuitry is configured to select the color Doppler image from the series of color Doppler images based on the generated index.

* * * * *